US010799341B2

(12) United States Patent
Remenschneider et al.

(10) Patent No.: US 10,799,341 B2
(45) Date of Patent: Oct. 13, 2020

(54) EAR CANAL GRAFTS

(71) Applicant: Massachusetts Eye and Ear Infirmary, Boston, MA (US)

(72) Inventors: Aaron K. Remenschneider, Boston, MA (US); Elliott Kozin, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 16/333,698

(22) PCT Filed: Sep. 14, 2017

(86) PCT No.: PCT/US2017/051501
§ 371 (c)(1),
(2) Date: Mar. 15, 2019

(87) PCT Pub. No.: WO2018/053087
PCT Pub. Date: Mar. 22, 2018

(65) Prior Publication Data
US 2019/0224003 A1 Jul. 25, 2019

Related U.S. Application Data

(60) Provisional application No. 62/395,647, filed on Sep. 16, 2016.

(51) Int. Cl.
*A61F 2/18* (2006.01)
*A61L 27/26* (2006.01)
(Continued)

(52) U.S. Cl.
CPC .............. *A61F 2/18* (2013.01); *A61F 11/004* (2013.01); *A61K 38/1808* (2013.01);
(Continued)

(58) Field of Classification Search
CPC .................................. A61F 2/18; A61F 11/002
(Continued)

(56) References Cited

U.S. PATENT DOCUMENTS

| 4,014,971 A | 3/1977 | Rodney |
| 5,007,934 A | 4/1991 | Stone |

(Continued)

FOREIGN PATENT DOCUMENTS

| CN | 2162943 | 4/1994 |
| JP | S50-031693 | 3/1975 |

(Continued)

OTHER PUBLICATIONS

Barry III et al., "Direct-Write Assembly of 3D Hydrogel Scaffolds for Guided Cell Growth. Advanced Materials," 2009, 21:2407-10.
(Continued)

*Primary Examiner* — Suzette J Gherbi
(74) *Attorney, Agent, or Firm* — Fish & Richardson P.C.

(57) ABSTRACT

The devices described herein are used for holding an undelay graft and an overlay graft in place for repair a tympanic membrane. The devices include a post having a proximal end and a distal end; and first and second arms, each having a proximal end and a distal end. The distal end of the post is flexibly joined to the proximal end of the first arm and to the proximal end of the second arm. When the device is in a deployed configuration, the first arm and the second arm extend substantially perpendicularly from the post; and when the first arm and the second arm are clamped into a constrained configuration, the first arm and the second arm extend substantially parallel to a central axis of the post.

18 Claims, 9 Drawing Sheets

(51) Int. Cl.
  A61F 11/00     (2006.01)
  A61K 38/18     (2006.01)
  A61L 27/38     (2006.01)
  A61L 27/58     (2006.01)
(52) U.S. Cl.
  CPC ...... *A61K 38/1825* (2013.01); *A61K 38/1858* (2013.01); *A61K 38/1866* (2013.01); *A61L 27/26* (2013.01); *A61L 27/3852* (2013.01); *A61L 27/58* (2013.01); *A61F 2002/183* (2013.01); *A61F 2210/0004* (2013.01); *A61F 2230/0069* (2013.01); *A61F 2230/0082* (2013.01); *A61F 2250/0067* (2013.01); *A61L 2300/414* (2013.01); *A61L 2430/14* (2013.01)
(58) Field of Classification Search
  USPC .................................................. 623/9; 604/8
  See application file for complete search history.

(56) References Cited

U.S. PATENT DOCUMENTS

| | | | |
|---|---|---|---|
| 5,501,700 | A | 3/1996 | Hirata |
| 6,309,419 | B1 | 10/2001 | Eugene et al. |
| 8,197,433 | B2 | 6/2012 | Cohen |
| 8,480,610 | B1 | 7/2013 | Hill |
| 9,987,168 | B2 * | 6/2018 | Fritsch .................... A61F 11/00 |
| 2003/0018291 | A1 | 1/2003 | Hill et al. |
| 2005/0075733 | A1 * | 4/2005 | D'Eredita ............. A61F 11/002 623/10 |
| 2006/0142736 | A1 * | 6/2006 | Hissink ................. A61F 11/002 604/540 |
| 2008/0234817 | A1 | 9/2008 | Huettenbrink et al. |
| 2008/0268016 | A1 | 10/2008 | Fang et al. |
| 2012/0191030 | A1 * | 7/2012 | Avior .................... A61F 11/002 604/9 |
| 2013/0345722 | A1 | 12/2013 | Margulis |
| 2014/0012282 | A1 | 1/2014 | Michael |
| 2014/0094910 | A1 | 4/2014 | Steinhardt et al. |
| 2014/0194891 | A1 | 7/2014 | Shahoian |
| 2014/0257518 | A1 | 9/2014 | McAlpine et al. |
| 2014/0303728 | A1 | 10/2014 | Steinhardt et al. |
| 2017/0367893 | A1 * | 12/2017 | Loushin ................ A61F 11/002 |
| 2018/0263763 | A1 * | 9/2018 | Margulis .................... A61F 2/18 |

FOREIGN PATENT DOCUMENTS

| | | |
|---|---|---|
| JP | 2011-110204 A | 6/2011 |
| WO | WO 2011/142425 A1 | 11/2011 |
| WO | WO 2016/005946 | 1/2016 |
| WO | WO 2016154148 | 9/2016 |
| WO | WO 2018/053087 | 3/2018 |

OTHER PUBLICATIONS

Boedts et al., "A scanning electron-microscopic study of different tympanic grafts," Am J Otol, 1990, 11(4):274-7.
Calobrace, "The design and engineering of the MemoryShape breast implant." Plast Reconstr Surg, 2014, 134(3 Suppl): 10S-15S.
Cheng et al., "Motion of the surface of the human tympanic membrane measured with stroboscopic holography," Hear Res, 2010, 263(1-2):66-77.
Cheng et al., "Wave motion on the surface of the human tympanic membrane: holographic measurement and modeling analysis," J Acoust Soc Am, 2013, 133(2):918-37.
Cranford et al., "Nonlinear material behaviour of spider silk yields robust webs," Nature, 2012, 482(7383):72-6.
Decraemer et al., "Shape and derived geometrical parameters of the adult, human tympanic membrane measured with a phase-shift moire interferometer," Hear Res, 1991, 51(1):107-21.
Dvorak, et al., "Repair of chronic tympanic membrane perforations with long-term epidermal growth factor," Laryngoscope, 1995, 105(12 Pt 1): 1300-1304.
Ensari, "Effects of polylactic acid film on middle ear mucosa and cochlear function in Guinea pigs," Eur Arch Otorhinolaryilgol, 2015, 272(5): 1091-1097.
EP Extended Search Report in European Appln. No. 16769523.8, dated Oct. 25, 2018, 8 pages.
EP Extended Search Report in European Appln. No. 17851503.7, dated Sep. 9, 2019, 7 pages.
EP Office Action in Appln. No. 17851503.7, dated Sep. 30, 2019, 8 pages.
Fernandes, "Composite chondroperichondrial clip tympanoplasty: The 1-6, 7/1-7/6 triple "C" technique," Otolaryngology Head Neck Surgery, 2003, 128: 267-72.
Geckil et al., "Engineering hydrogels as extracellular matrix mimics," Nanomedicine (Lond), 2010, 5(3):469-84.
Gersdorff, et al., "Overlay versus underlay tympanoplasty. Comparative study of 122 cases," Rev Laryngol Otol Rhinol (Bord), 2003, 124(1): 15-22.
Ghanem, et al., "Butterfly cartilage graft inlay tympanoplasty for large perforations," Laryngoscope, 2006, 116(10): 1813-1816.
Gratson et al., "Microperiodic structures: direct writing of three-dimensional webs," Nature, 2004, 428(6981):386.
Hanson Shepherd et al,, "3D Microperiodic Hydrogel Scaffolds for Robust Neuronal Cultures," Adv Funct Mater, 2011, 21:47-54.
Hardman et al., "Tympanoplasty for Chronic Tympanic Membrane Perforation in Children: Systematic Review and Meta-analysis," Otol Neurotol. 2015, 36(5):796-804.
Hiraide et al., "The fiber arrangement of the pathological human tympanic membrane," Arch Otorhinolaryngol, 1980, 226(1-2):93-9.
Hod et al., "Inlay "butterfly" cartilage tympanoplasty," Am J Otolaryngol, 2013, 34(1): 41-43
Hong et al., "Repair of tympanic membrane perforation using novel adjuvant therapies: a contemporary review of experimental and tissue engineering studies," Int J Pediatr Otorhinolaryngol, 2013, 77(1): 3-12.
House et al., "Incus homografts in chronic ear surgery," Arch Otolaryngol, 1966, 84(2):148-53.
Jang et al., "Regeneration of chronic tympanic membrane perforation using 3D collagen with topical umbilical cord serum," International Journal of Biological Macromolecules, 2013, 62: 232-240.
Kaylie et al., "Revision chronic ear surgery," Otolatyngol Head Neck Surg, 2006, 134(3):443-50.
Khanna and Tonndorf, "Tympanic membrane vibrations in cats studied by time-averaged holography," J Acoust Soc Am, 1972, 51:1904-20.
Kim et al., "Functional and Practical Outcomes of Inlay Butterfly Cartilage Tympanoplasty." Otol Neurotol, 2014, 35: 1458-1462.
Kohn et al., "New perspectives in myringoplasty," Int J Artif Organs, 1984, 7(3):151-62.
Kozin et al., "Design, fabrication, and in vitro testing of novel three-dimensionally printed tympanic membrane grafts," Hear Res, Oct. 2016, 340: 191-203.
Kozin et al., Theoretical and Practical Considerations of 3-Dimensionally Printed Biomimetic Tympanic Membrane Grafts: Preliminary Design, Manufacture, and Acoustic Testing. Middle Ear Mechanics and Research in Otology, 2015, M. Gaihede. Aalborg, Denmark, MEMRO, 3 pages.
Levin et al., "Preliminary results of the application of a silk fibroin scaffold to otology," Otolaryngology—Head and Neck Surgery, Mar. 2010, 142(3_suppl):S:33-5.
Levin et al., "Grafts in myringoplasty: utilizing a silk fibroin scaffold as a novel device," Expert Rev Med Devices, 2009, 6(6):653-64.
Lewis, "Direct Ink Writing of 3D Functional Materials," Advanced Functional Materials, 2006, 16:2193-204.
Lim, "Structure and function of the tympanic membrane: a review," Acta oto-rhino-laryngologica Belgica, 1995, 49(2):101-I5.
Lukasiak et al., "Biodegradation of Silicones (Organosiloxanes)," 2005, 52 pages.
Marquet, "Human middle ear transplants," J Laryngol Otol, 1971, 85(6):523-39.
Minoda et al., "External auditory canal stenting utilizing a useful rolled, tapered silasticsheet (RTSS) post middle ear surgery," Auris Nasus Larynx, 2010, 37(6): 680-684.

(56) References Cited

OTHER PUBLICATIONS

Mironov et al,, "Organ printing: computer-aided jet-based 3D tissue engineering," Trends in Biotechnology, 2003, 21(4):157-61.
Tota et al., "Multiscale fabrication of biomimetic scaffolds for tympanic membrane tissue engineering," Biofabrication, May 2015, 7: 025005.
Murphy and Atala, "3D bioprinting of tissues and organs," Nat Biotechnol, 2014, 32(8):773-85.
Nadol et al., "Cellular immunologic responses to cochlear implantation in the human," Hear Res, 2014, 318: 11-17.
Parekh et al., "Repair of the tympanic membrane with urinary bladder matrix," Laryngoscope, 2009, 119(6): 1206-1213.
Park et al., "Predictors for outcome of paper patch myringoplasty in patients with chronic tympanic membrane perforations," Eur Arch Otorhinolatvngol, 2015, 272(2): 297-301.
PCT International Preliminary Report on Patentability in international Application No. PCT/US2016/023482, dated Jun. 20, 2016, 9 pages.
PCT International Preliminary Report on Patentability in international Application No. PCT/US2017/051501, dated Mar. 19, 2019, 8 pages.
PCT International Search Report and Written Opinion in International Application No. PCT/US16/23482, dated Jun. 20, 2016, 10 pages.
PCT International Search report and Written Opinion in International Application No. PCT/US2017/051501, dated Nov. 29, 2017, 14 pages.
Pfaltz and Griesemer, "Pericard: a new biometerial for tympanoplasty: preliminary report," Am J Otolaryngol, 1985, 6(3):266-8.
Qin et al., "Structural optimization of 3D-printed synthetic spider webs for high strength. Nature communications," 2015, 6:7038.
Rosowski et al., "Computer-assisted time-averaged holograms of the motion of the surface of the mammalian tympanic membrane with sound stimuli of 0.4-25 kHz," Hear Res, 2009, 253(1-2):83-96.
Rosowski et al., "New data on the motion of the normal and reconstructed tympanic membrane," Otol Neurotol, 2011, 32(9):1559-67.
Sehktar, "Designing cell-compatible hydrogels for biomedical applications," Science, 2012, 336(6085):1124-8.
Seyyedi and Nadol, Jr., "Intracochlear Inflammatory Response to Cochlear Implant Electrodes in Humans," Otol Neurotol, 2014, 35: 1545-1551.
Shimada and Lim, "The fiber arrangement of the human tympanic membrane. A scanning electron microscopic observation," Ann Otol Rhinol Laryngol, 1971, 80(2):210-7.
Sun et al., "Direct-Write Assembly of 3D Silk/hydroxyapatite Scaffolds for Bone Co-Cultures," Advanced Healthcare Materials, 2012, 1:729-35.
Tamimi et al., "Osseointegration of dental implants in 3D-printed synthetic onlay grafts customized according to bone metabolic activity in recipient site," Biomaterials, 2014, 35(21): 5436-5445.
Teh et al., "Tissue Engineering of the 2-12,14 Tympanic Membrane," Tissue Engineering Part B: Reviews, Apr. 1, 2013, 19(2): 116-32.
Tonndorf and Khanna, "The role of the tympanic membrane in middle ear transmission," Ann Otol, 1970, 79:743-53.
Tonndorf and Khanna, "Tympanic-membrane vibrations in human cadaver ears studied by time-averaged holography," J Acoust Soc Am, 1972, 52:1221-33.
Uebersax et al., "Biocompatibility and osteoconduction of macroporous silk fibroin implants in cortical defects in sheep," Eur J Norm Biopharm, 2013, 85(1):107-18.
Ulku et al., "Comparisons of the mechanics of partial and total ossicular replacement prostheses with cartilage in a cadaveric temporal bone preparation," Acta Otolmyngol, 2014, 134(8):776-84.
Villar-Fernandez et al., "Outlook for tissue engineering of the tympanic membrane," Audiology Research, Jan. 2015, 5: 117.
Weber et al., "Tissue-engineered calcium alginate patches in the repair of chronic chinchilla tympanic membrane perforations," Laryngoscope, 2006, 116(5): 700-704.
Wehrs, "Grafting techniques," Otolaryngol Clin North Am, 1999, 32(3): 443-455.
Wieland et al., "Poly(glycerol sebacate)-engineered plugs to repair chronic tympanic membrane perforations in a chinchilla model," Otolaryngol Head Neck Sung, 2010, 143(1): 127-133.
Wrzeszcz, et al., "Hydrogel coated and dexamethasone releasing cochlear implants: quantification of fibrosis in guinea pigs and evaluation of insertion forces in a human cochlea model," J Biomed Mater Res B Appl Biomater, 2015, 103(1): 169-178.
Zhang and Gan, "A comprehensive model of human ear for analysis of implantable hearing devices," IEEE Trans Biomed Eng, 2011, 58(10):3024-7.
AU Office Action in AU Application No. 2016235333, dated Jan. 15, 2020, 5 pages.
JP Office Action in Japanese Appln. No. 2017-549395, dated Jan. 7, 2020, 15 pages (with English translation).
PCT International Search report and Written Opinion in International Application No. PCT/US2016/023482, dated Jun. 20, 2016, 14 pages.

* cited by examiner

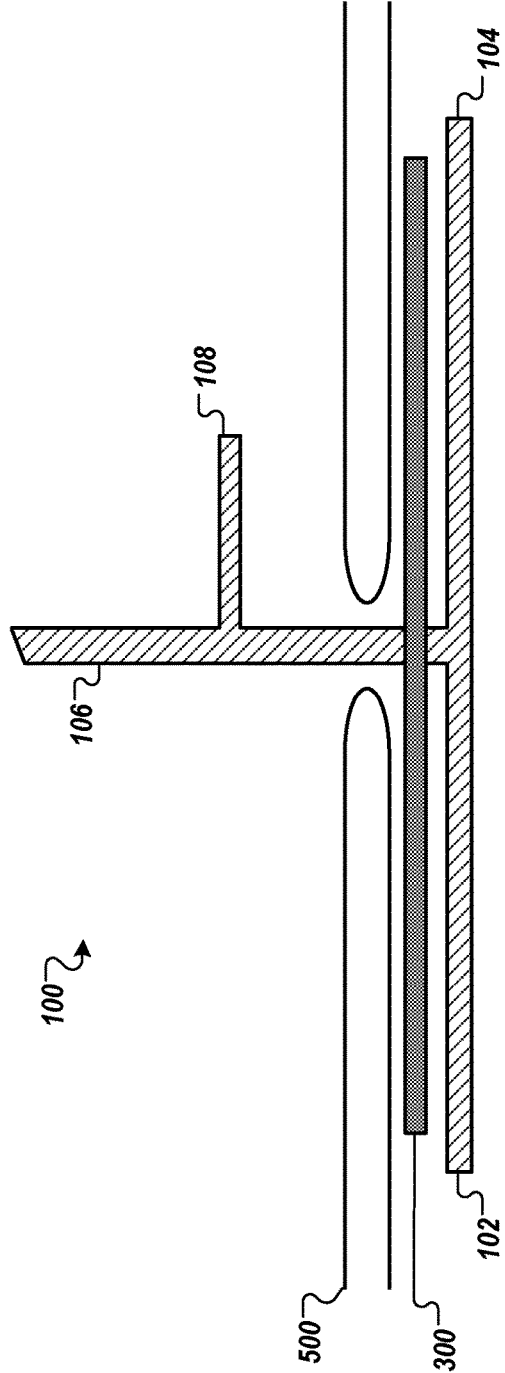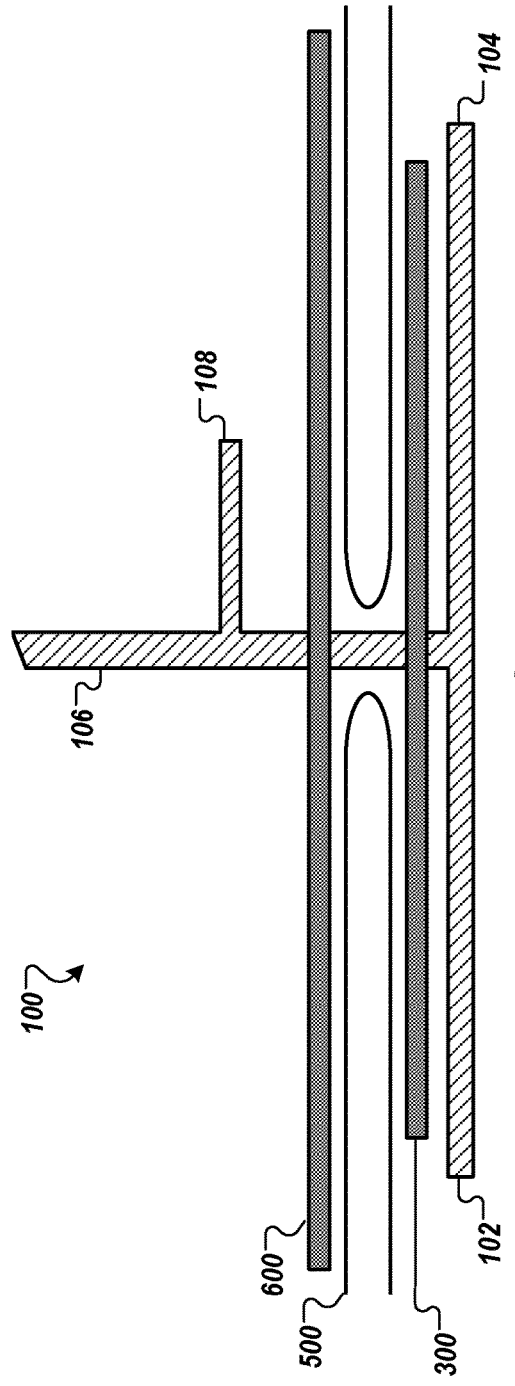

EAR CANAL GRAFTS

CLAIM OF PRIORITY

This application is a 371 U.S. National Phase Application of PCT/US2017/051501, filed on Sep. 14, 2017, which claims the benefit of U.S. Provisional Patent Application Ser. No. 62/395,647, filed on Sep. 16, 2016. The content of the foregoing application is hereby incorporated by reference in its entirety.

FIELD OF THE INVENTION

The invention relates to ear canal grafts.

BACKGROUND OF THE INVENTION

Diseases of the middle ear, such as chronic suppurative otitis media (CSOM), are common in children and adults. CSOM affects more than 30 million individuals worldwide annually, leading to a health care burden of as much as $10,000 per patient per year. The most frequent long-term complication in patients with CSOM is persistent tympanic membrane perforation and conductive hearing loss. These complications are surgically correctable via tympanoplasty, which is a common procedure. There are roughly 150,000 tympanoplasty procedures performed year in the United States. The goals of tympanoplasty are to recreate a robust barrier between the canal and middle ear, as well as to reestablish sound transmission to the ossicular chain in a fashion similar to the native tympanic membrane. Typically, tympanoplasty requires patients to be placed under general anesthesia. Surgery can take between 2-3 hours and requires grafting of the eardrum using biologic or biocompatible materials. Materials must maintain their position following surgical placement to ensure successful results. Healing times following surgical tympanoplasty range between 4-8 weeks and wound hearing results are highly variable. Inadequate outcomes are due to displacement of grafts during the healing process and or poor approximation of grafts to the perforation and remnant tympanic membrane.

SUMMARY OF THE INVENTION

In one aspect, this disclosure features devices for holding an undelay graft and an overlay graft in place for repair of a tympanic membrane. The devices include a post having a proximal end and a distal end; and first and second arms, each having a proximal end and a distal end. The distal end of the post is flexibly joined to the proximal end of the first arm and to the proximal end of the second arm. When the device is in a deployed configuration, the first arm and the second arm extend substantially perpendicularly from the post; and when the first arm and the second arm are clamped into a constrained configuration, the first arm and the second arm extend substantially parallel to a central axis of the post.

Implementations of the new devices can include any combination, one, all, or none of the following features. For example, the devices can include a shelf having a proximal end and a distal end, wherein the proximal end of the shelf is joined to the post between the proximal and distal ends such that, when the device is in a deployed configuration, the shelf extends substantially perpendicularly from the post and is substantially perpendicular to the first arm and the second arm.

The devices can include one or more biodegradable materials. For example, the devices can include or be made of at least one or more of polydimethylsiloxane (PDMS), hyaluronic acid (HA), poly(glycolic acid) (PGA), poly (lactic-co-glycolic acid) (PLGA), polylactic acid (PLA), polyurethane, poly(ester urethane)urea (PEUU), poly(carbonate urethane) urea (PECUU), collagen, fibrin, nylon, silk, poliglecaprone, and elastin. The devices can further include at least one of a cellular adhesion-inducing material and a cellular invasion-inducing material. The devices can also include one or more living cells, such as living fibroblasts, chondrocytes, keratinocytes, and/or epithelial cells, in a scaffold material that enables the cells to thrive and reproduce once implanted.

In some embodiments, the devices include one or more growth factors. The growth factors can be one or more of fibroblast growth factor (FGF), vascular endothelial growth factor (VEGF), and platelet-derived growth factor (PDGF), and epidermal growth factor (EGF). The devices can also include one or more of a drug and drug eluting material.

In another aspect, the disclosure features methods of repairing a perforation in a tympanic membrane. The methods include loading an underlay graft on one of the devices described herein; clamping the first and second arms into the constrained configuration to cause the first and second arms to extend substantially parallel to a central axis of the post; passing i) the first arm, ii) the second arm, iii) the distal end of the post, and iv) the underlay graft from a lateral side of the tympanic membrane to a medial side of the tympanic membrane through the perforation; releasing the first and second arms from the constrained configuration to hold the underlay graft in contact with a medial surface of the tympanic membrane; and loading the overlay graft onto the post of the device, which extends out through the perforation into the ear canal, such that the overlay graft is in contact with the lateral side of the tympanic membrane.

Implementations of the new methods can include any combination, one, all, or none of the following features. The methods can include removing the device by pulling the post member out through the remaining perforation after the tympanic membrane has healed at least a portion of the perforation. In some embodiments, the methods can include dissolving the device by application of a dissolving agent. The methods can also include solidifying the device by application of a solidifying agent. Loading the underlay graft on the device can include passing the distal end of the post through a hole in the underlay graft.

The devices used in these methods can further include a shelf having a proximal end and a distal end, wherein the proximal end of the shelf is joined to the post between the proximal and the distal ends such that, when the device is in a deployed configuration, the shelf extends substantially perpendicularly from the post and is substantially perpendicular to the first arm and the second arm.

In another aspect, the disclosure features systems for holding an underlay graft and an overlay graft in place for repair of a tympanic membrane. The systems include the devices described herein and an underlay graft that includes a hole that can be loaded onto the post of the device such that the post passes through the hole. The system can include an overlay graft comprising a second hole. In some implementations, the overlay graft is loaded onto the device such that the post passes through the second hole. The devices can include a shelf having a proximal end and a distal end, wherein the proximal end of the shelf is joined to the post between the proximal end and the distal end of the post such that, when the device is in a deployed configuration, the shelf extends substantially perpendicularly from the post and is substantially perpendicular to the first arm and the second arm. The underlay graft can rest on the post between i) the shelf and ii) the first arm and the second arm.

The devices used in these new systems can include one or more biodegradable materials. For example, the devices can include or be made of at least one or more of polydimethylsiloxane (PDMS), hyaluronic acid (HA), poly(glycolic acid) (PGA), poly (lactic-co-glycolic acid) (PLGA), polylactic acid (PLA), polyurethane, poly(ester urethane)urea (PEUU), poly(carbonate urethane) urea (PECUU), collagen, fibrin, nylon, silk, poliglecaprone, and elastin. The devices can further include at least one of a cellular adhesion-inducing material and a cellular invasion-inducing material. The devices can also include one or more living fibroblasts, chondrocytes, keratinocytes, and/or epithelial cells in a scaffold material that enables the cells to thrive and reproduce once implanted.

In some embodiments, the devices used in the systems include one or more growth factors. The growth factors can be one or more of fibroblast growth factor (FGF), vascular endothelial growth factor (VEGF), and platelet-derived growth factor (PDGF), and epidermal growth factor (EGF). The devices can also include one or more of a drug and drug eluting material.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 9A-9D are a series of schematic diagrams that show a cross-sectional view of an example of a bilayer tympanic membrane insertion device in use.

DETAILED DESCRIPTION

Bilayer tympanic membrane insertion devices are described herein, along with some processes for manufacturing such devices, and uses of such devices.

Bilayer Tympanic Membrane Graft Insertion Devices

The bilayer tympanic membrane graft insertion devices described herein are used to hold a tympanic membrane underlay graft and a tympanic membrane overlay graft against a tympanic membrane in a tympanoplasty procedure to ensure proper contact, adhesion, improved sound transmission, and healing of the membrane after trauma or disease causes a perforation. This device has a general "T" shape, and is made of a safe, i.e., biologically inert, and flexible material so that the arms of the T can be held together in a constrained configuration with forceps or other tools. In the constrained configuration, the arms and underlay graft can be passed through a perforation in a tympanic membrane and released. Once released, the device returns to a deployed configuration in a state of rest, extending the arms and thereby holding the underlay graft against the medial (internal) side of the tympanic membrane. An overlay graft can be placed onto the post of the device, and thereby held into place against the lateral (external) side of the tympanic membrane.

The device may be left in place while the subject's tympanic membrane heals. The device can later be removed or may dissolve, or be dissolved, in place over time, for example, once the tympanic membrane has healed sufficiently, and the remaining pinpoint hole in the membrane after removal of the device will then heal completely to close the entire perforation.

Figure 1:
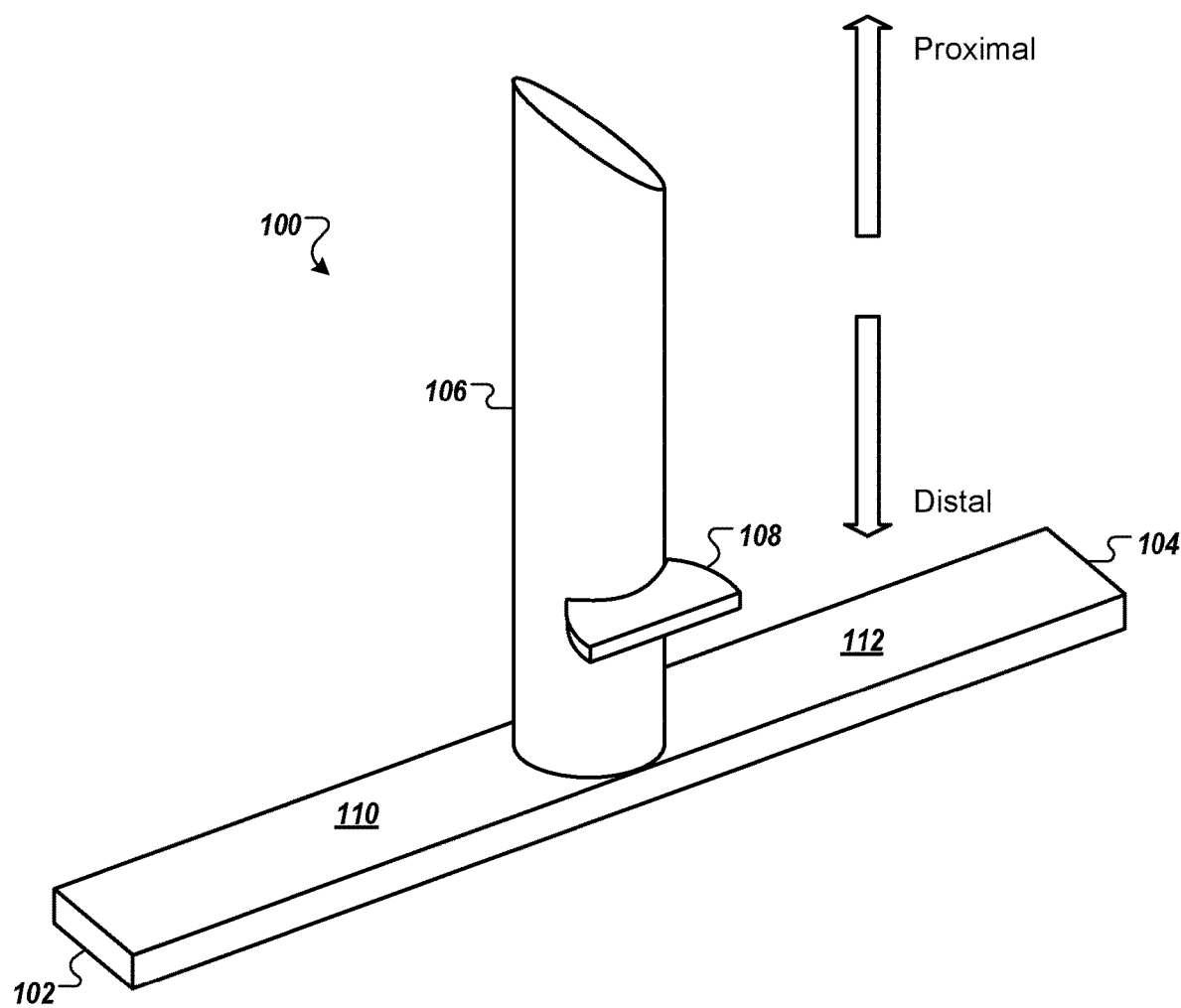
FIG. 1 is an isometric view of an example of a bilayer tympanic membrane graft insertion device.

FIG. 1 is an isometric view of an example of a bilayer tympanic membrane graft insertion device 100. The device 100 is formed in a "T" shape, having two arms 102 and 104 that extend substantially perpendicularly from a post 106. The device 100 also includes a shelf 108 that extends substantially perpendicularly from the post 106. The shelf 108 may or may not align with the arms 102 and 104. Each of the elements of the "T" shape can be manufactured separately and then connected together, e.g., using adhesives such as fibrin glue or cyanoacrylate, hot melting, friction-fit, or one or more of the elements can be manufactured in one piece, or all of the elements can be manufactured in one piece.

Figure 3:
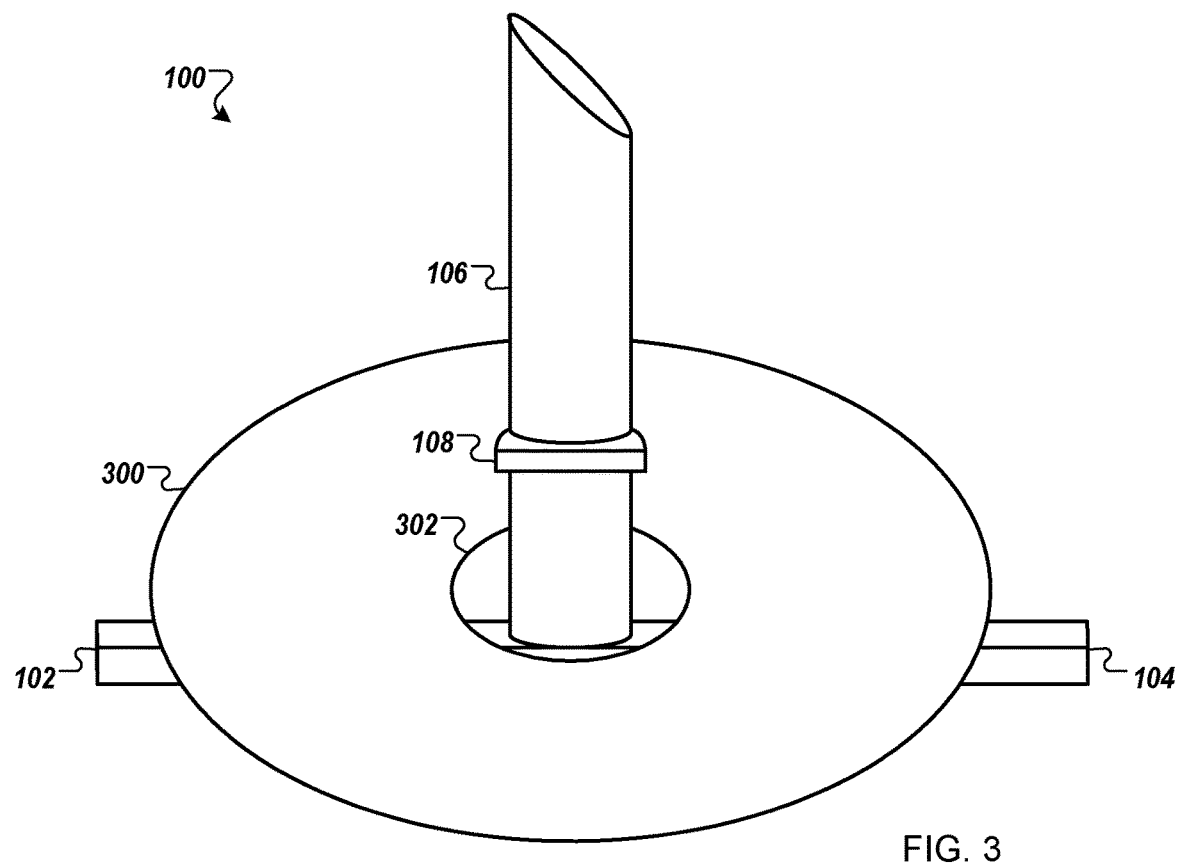
FIG. 3 is a schematic diagram that shows an example of a bilayer tympanic membrane graft insertion device loaded with a tympanic membrane underlay graft.
Figure 4:
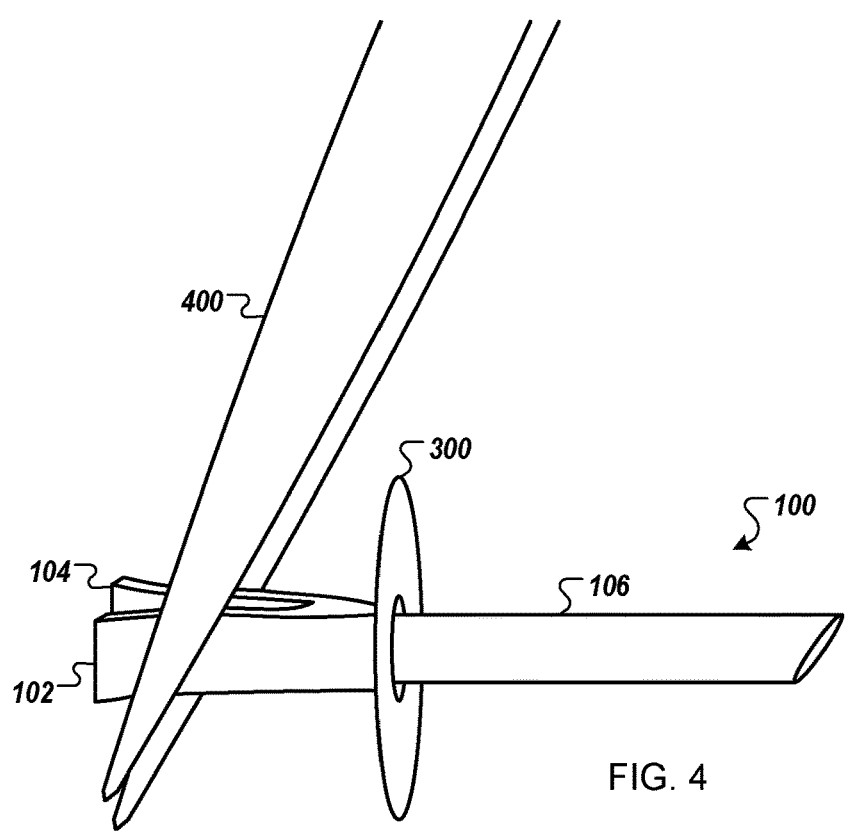
FIG. 4 is a schematic diagram that shows an example of a bilayer tympanic membrane graft insertion device in a constrained configuration.

The arms 102 and 104 include contact surfaces 110 and 112, respectively. As will be described below and shown in FIG. 3, the contact surfaces 110 and 112 can come into contact with an underlay graft when an underlay graft is loaded onto the device 100. In addition, the contact surfaces 110 and 112 may also be held by a tool such as a forceps to bend the arms 102 and 104, as shown in FIG. 4. When the device 100 is in the shape shown in FIG. 1, the device 100 will be referred to as being in a "deployed configuration." When the device 100 is clamped as shown in FIG. 3, the device 100 will be referred to as being on a "constrained configuration."

As used herein, "substantially perpendicular" is used to mean that the surfaces provide purchases for a graft to prevent the graft from moving along the post 106 past a substantially perpendicular feature. Thus, substantially perpendicular can include 90 degrees, 90+/−1 degrees, or 90+/−2, 3, 4, 5, 6, 7, 8, 9, 10, 15, or 20 degrees. While the device shown is in a perpendicular configuration, the surfaces (102/104) may be configured at an angle tailored to the patient's specific anatomy.

As used here, the end of the device 100 that will be nearest to the clinician is referred to as the proximal end of the device 100. The end of the device 100 that will be farthest away from the clinician is referred to as the distal end of the device 100. Once placed, the distal end of the device 100 will be on the medial (internal, middle ear) side of the patient's tympanic membrane, and the proximal end of the device 100 will be on the lateral (external, ear canal) side of the patient's tympanic membrane.

Figure 2A:
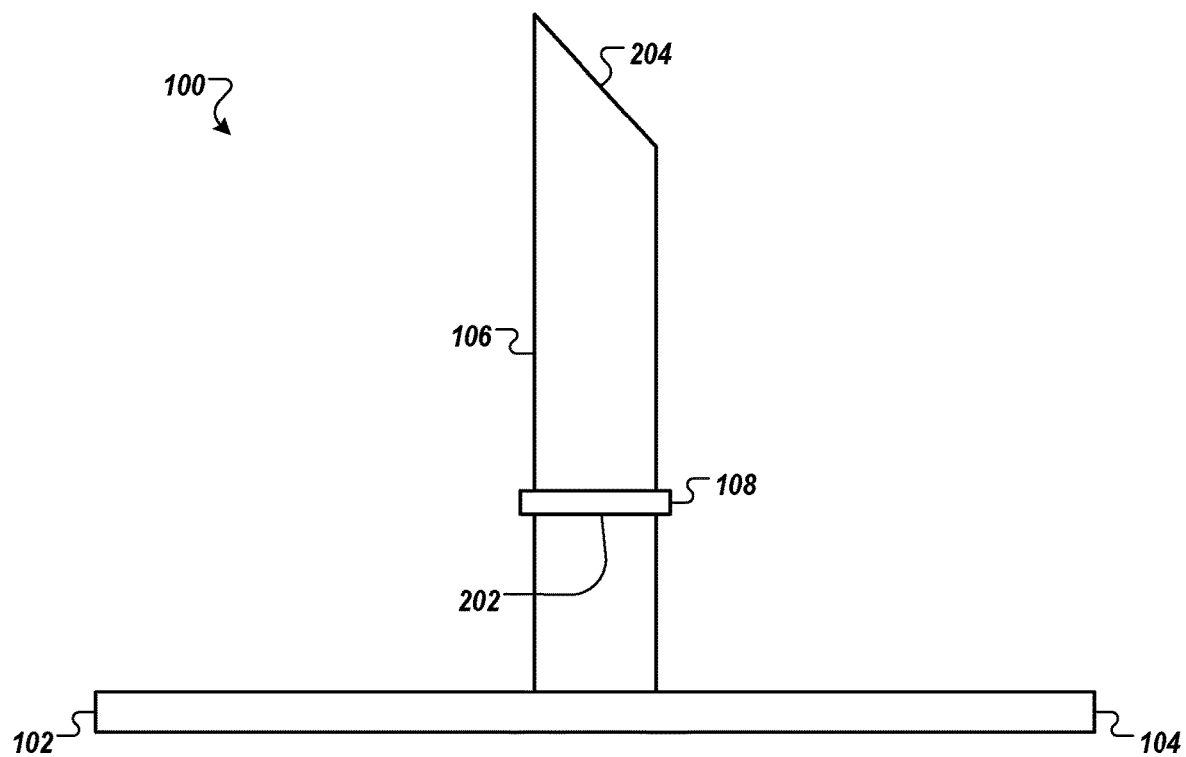
FIGS. 2A and 2B are side views of two examples of bilayer tympanic membrane graft insertion device.
Figure 2B:
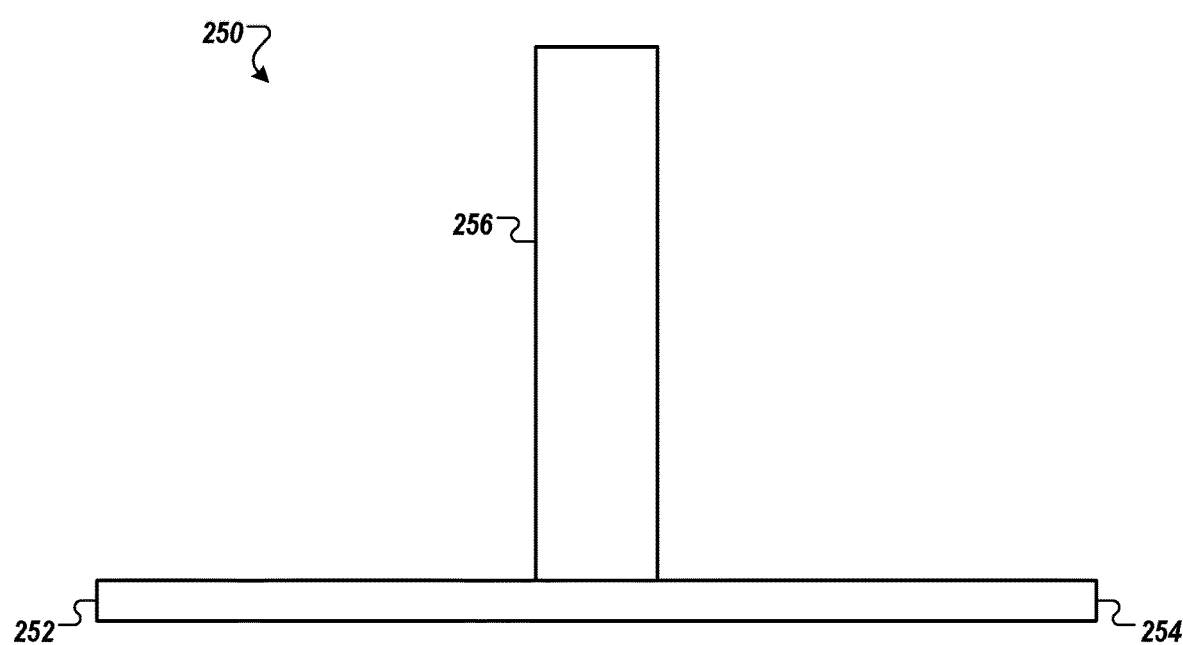

FIGS. 2A and 2B are side view of two examples of two different bilayer tympanic membrane graft insertion devices. In FIG. 2A, the device 100 is shown with the shelf 108 and an angled top 204. In FIG. 2B, a device 250 is shown, and the device 250 does not include a shelf or an angled top. The two features can be included on the device, or not, independently.

As shown in FIG. 2A, shelf 108 of the device 100 includes a contact surface 202. In general, the shelf 108 is used to hold underlay and overlay grafts in place on the post 106, to prevent the grafts from backing off the post 106, and to become displaced or compromise the repair. As will be described below with respect to FIGS. 7A to 7D, the contact surface 202 can contact an overlay graft when the overlay graft is loaded onto the device 100.

Figure 6:
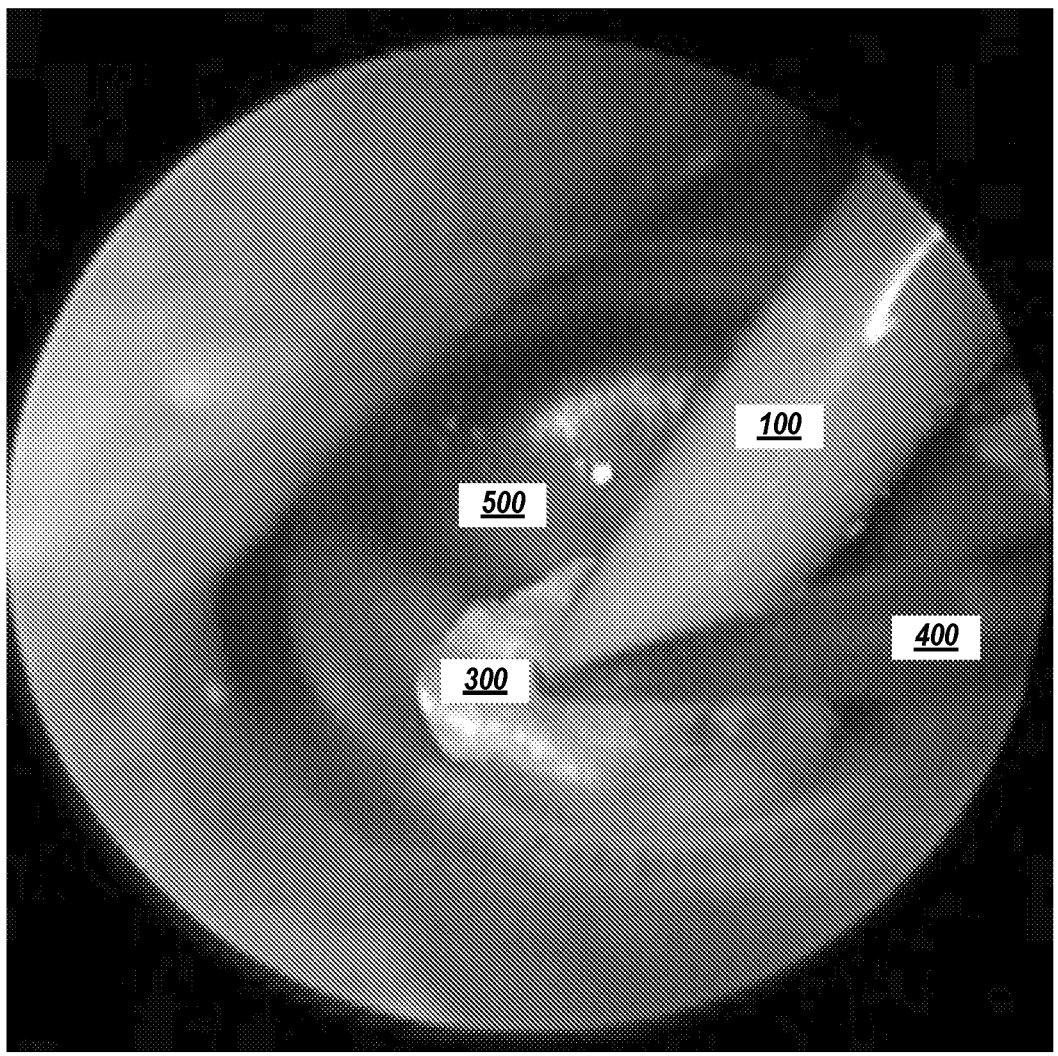
FIG. 6 is an endoscopic view of a tympanoplasty in which the arms of an example of a bilayer tympanic membrane graft insertion device and a tympanic membrane underlay graft are being placed through a perforation of a tympanic membrane.

The post 106 can include an angle top 204. The angled top can be useful, for example, in instances where the post 106 is of sufficient length that it may contact the skin of the external auditory canal. The angle top 204 allows for a longer post 106 while avoiding trauma and discomfort of the ear canal skin, as shown in FIG. 6 below.

The device 250 includes arms 252 and 254, with a post 256, and without a shelf or angled top. The shelf may not be needed, for example, in instances when grafts are unlikely to back off the post 106. The device 250 is also shown without an angled top. The angled top may not be needed, for example, in instances when a shorter post is appropriate, or when the anatomy of the ear canal does not oblige an angled post for avoiding contact with the ear canal skin. Other configurations that can be used in addition or in lieu of the shelf or shelf 108 to prevent back migration of the grafts include a fabricated rough surface of the post 106 or a notched surface of the post 106 or a series or corrugations of the post.

Methods of Using Bilayer Tympanic Membrane Graft Insertion Devices

The devices described herein can be used for any appropriate tympanoplasty operations for the reconstruction or repair of a patient's tympanic membrane, including for use in both human and non-human patients. In many procedures, access to the tympanic membrane is through the ear canal itself, serving as a surgical portal, or an incision can be made behind or in front of the ear to access a tympanic membrane in need of repair with a graft. These incisions can be an endaural incision or a postauricular incision. Once access to the patient's tympanic membrane is achieved, the native (diseased or remnant) tympanic membrane can be repaired.

Performing a tympanoplasty with the device 100 comprises the steps of loading an underlay graft onto the post of device 100; clamping the device 100 to cause the arms to extend into the constrained configuration; passing the arms, the distal end of the post, and the underlay graft through a perforation in the tympanic membrane to the medial side of the tympanic membrane; and then loading an overlay graft on the device 100 to be in contact with the lateral side of the tympanic membrane. Later, after the tympanic membrane has healed sufficiently, the device 100 can be removed or dissolved. To aid in this healing, the device 100 can be drug eluting to provide, for example, steroids, antibiotics, or growth factors such as, for example, vascular endothelial growth factor (VEGF).

FIG. 3 shows the device 100 loaded with a tympanic membrane underlay graft 300. For example, a clinician can hold the device 100 with a pair of forceps (FIG. 4), or the device 100 and the graft 300 with a single pair of forceps. This places the device in the constrained configuration. The device 100 and graft 300 are passed through the perforation in the tympanic membrane and the surfaces are released. The device 100 will then resume the deployed configuration. Following release of the device 100, the surfaces 102 and 104 act to hold the underlay graft against the remnant tympanic membrane. Placing the underlay graft 300 on the device 100 generally occurs outside of the patient's body as a "loading step."

The underlay graft 300 can be made from any suitable material for use in a tympanoplasty procedure. This includes allografts (such as temporalis fascia, perichondrium, or fat), xenografts, as well as biological, bioresorbable, biodegradable, or bioabsorbable materials. The underlay graft 300 can be formed in a circular shape as shown here, or in any other shape as desired by the clinician and based on available graft material and shape of the perforation to be repaired.

FIG. 4 shows the device 100 in a constrained configuration. For example, the clinician may use a pair of forceps 400, or another appropriate tool, to squeeze the arms 102 and 104 together so that the arms 102 and 104 extend, e.g., substantially parallel, with respect to the post 106. The forceps 400 can be a locking type of forceps, or they can be held in place by the clinician to clamp the arms 102 and 104.

As used here, substantially parallel is used to mean that the arms 102 and 104 are more parallel than perpendicular with the post 106. Thus, substantially perpendicular can include 90 degrees, 90+/−1 degrees, or 90+/−20 degrees.

Figure 5:
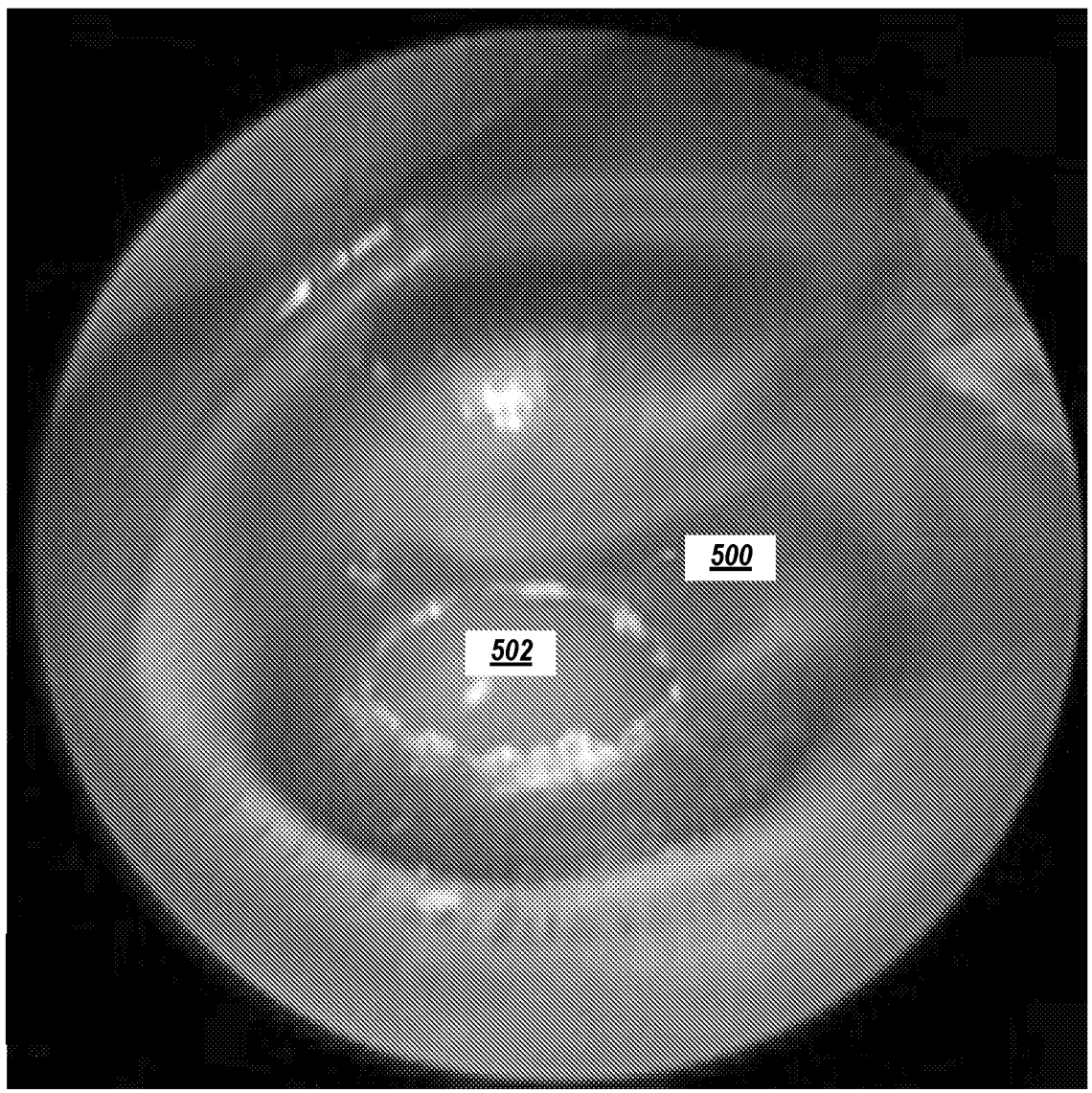
FIG. 5 is an endoscopic view of a tympanic membrane with a perforation.

FIG. 5 is an endoscopic view of a tympanic membrane 500 with a perforation 502. The view of FIG. 5 can be seen, for example, by a clinician using an endoscope during the tympanoplasty.

FIG. 6 is an endoscopic view of a tympanoplasty in which the arms of an example of a bilayer tympanic membrane graft insertion device 100 and a tympanic membrane underlay graft 300 are being placed through a perforation 502 of a tympanic membrane 500. The view of FIG. 6 can be seen, for example, by a clinician using an endoscope during the tympanoplasty. Shown here is the device 100 in the constrained configuration and clamped by the forceps 400 and the underlay graft 300 loaded on the device 100. Also shown here is the tympanic membrane 500.

Using the forceps 400 or other appropriate tools, the clinician passes the distal end of the device 100 and the underlay graft 300 through the perforation 504 of the tympanic membrane 500. The clinician can then unclamp the device 100, allowing the device 100 to return to the deployed configuration in which the arms 102 and 104 extend substantially perpendicular from the post 106. In doing so, the arms 102 and 104 are now able to hold the underlay graft 300 against the medial side of the tympanic membrane 500. This may require additional adjustment to the placement of the graft 300 and/or device 100 by the clinician, for example by grasping and moving the post 106 with the forceps 400.

Figure 7:
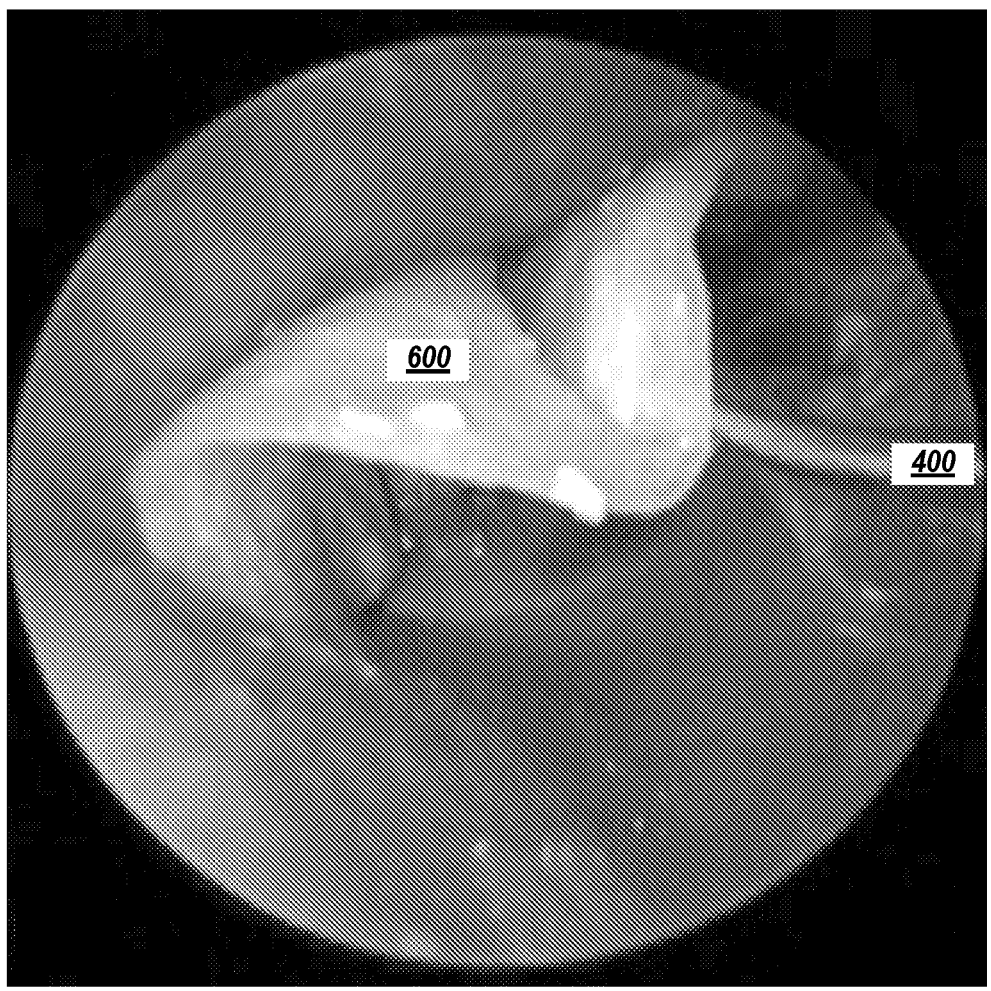
FIG. 7 is an endoscopic view of a tympanoplasty in which a tympanic membrane overlay graft is being loaded onto a post of an example of a bilayer tympanic membrane graft insertion device.

FIG. 7 is an endoscopic view of a tympanoplasty in which a tympanic membrane overlay graft is being loaded onto a post of an example of a bilayer tympanic membrane graft insertion device 100. The view of FIG. 7 can be seen, for example, by a clinician using an endoscope during the tympanoplasty. Shown here, the clinician is using forceps 400 to position the overlay graft 600 so that the post 106 (not seen in this view) passes through a hole (not seen in this view) in the center of the overlay graft 600.

Figure 8:
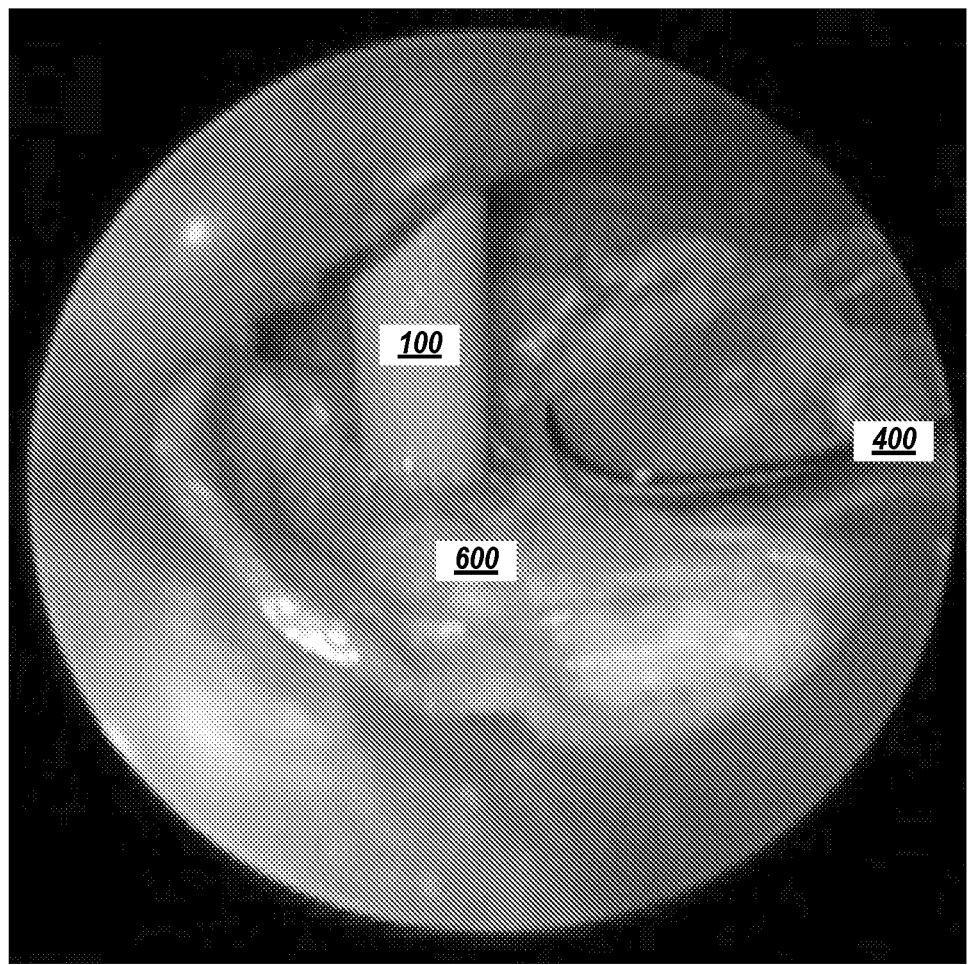
FIG. 8 is an endoscopic view of a tympanoplasty in which a tympanic membrane overlay graft has been placed onto the post and pushed against the tympanic membrane.

FIG. 8 is an endoscopic view of a tympanoplasty in which a tympanic membrane overlay graft 600 has been placed onto the post and pushed against the tympanic membrane 500. Shown here is the device 100, with an overlay graft 600 loaded. The overlay graft 600 has been loaded by the clinician using the forceps 400, and placed in contact with the lateral side of the tympanic membrane.

Later, after the patient's tympanic membrane has had time to heal, e.g., by growing membrane tissue to seal the perforation and to seal against and grow into the grafts 300 and 600, the device 100 can be removed. In some cases, this can be accomplished by a clinician pulling on the post 106 of the device 100 with an appropriate tool such as forceps 400. In some cases, a clinician may apply a dissolving agent to dissolve the device 100. However, in some cases, removal may not be required. For example, the device 100 can be made of a biodegradable or bioabsorbable material, e.g., in situations in which it is determined that a particular patient's circumstances prevent or counsel against removal. In some such cases, a clinician may apply a solidifying compound to solidify the device 100.

Figure 9A:
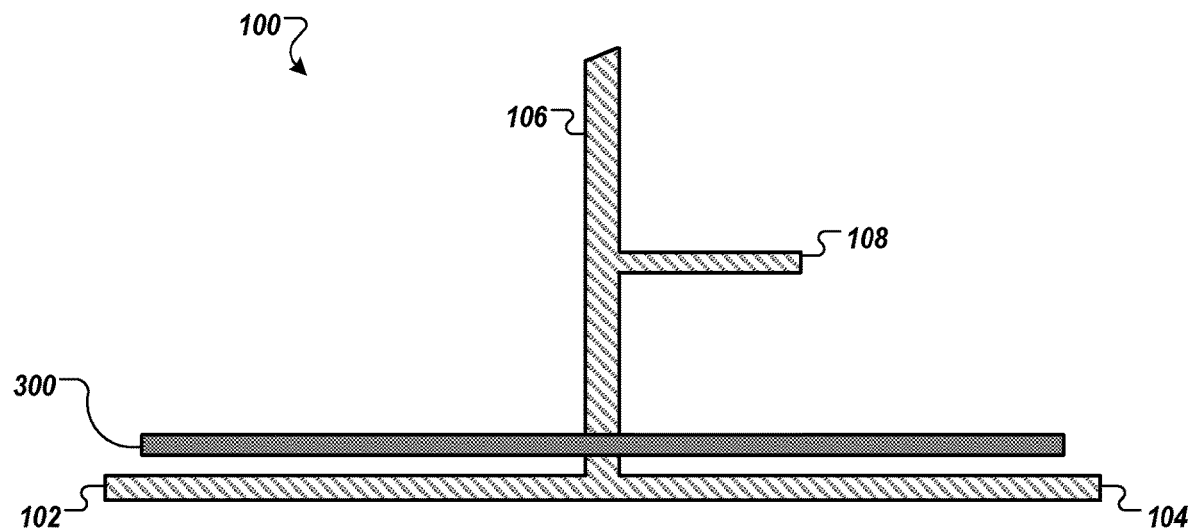
Figure 9B:
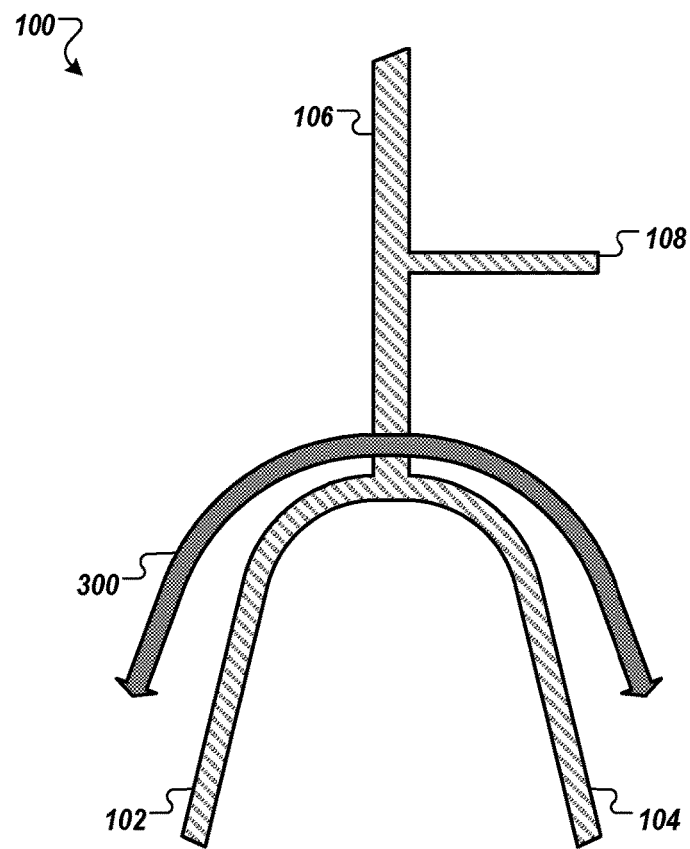

FIGS. 9A-9D are a series of schematic diagrams that show a cross-sectional view of an example of a bilayer tympanic membrane graft insertion device in use. In FIG. 9A, the device 100 is shown with the underlay graft 300 loaded onto the device 100, for example as described with respect to FIG. 3. In FIG. 9B, the device 100 has been clamped into the start of a constrained configuration, for example as described with respect to FIG. 4. Ultimately, the underlay graft may be rolled up or furled around the constrained, extending arms so that this entire part of the loaded device can be inserted through the perforation in the tympanic membrane. In FIG. 9C, the device 100 is shown placed in the perforation of the tympanic membrane 500, for example as described with respect to FIG. 4. In FIG. 9C, the device 100 is shown with the overlay graft 300 loaded onto the device 100, for example as described with respect to FIG. 6. FIG. 9D shows the device 100 after it has been placed by a clinician.

In this example, the diameter of the underlay graft 300 is less than the length of the arms, allowing the underlay graft 300 to be supported by the arms 102 and 104. In other configurations, the graft can be larger in diameter than the length of the two arms. In addition, the two arms can be of different lengths. In general, as further shown in FIG. 9D, the tympanic membrane 500 contacts the underlay graft 300, with the medial side of the tympanic membrane 500 contacting the underlay graft 300 and with the lateral side of the tympanic membrane 500 contacting the overlay graft 600.

In addition to the shapes shown in the FIGS. 1-7, other bilayer tympanic membrane graft insertion devices may function the same or similarly with different geometry. For example, some devices may have hollow posts, may have more arms or arms of different shapes, and may have different proportions than shown. Further, the shape of a device 100 may be altered by a clinician before or during use. For example, for a pediatric patient or a patient with a small defect, the length of the arms 102 and 104 and/or post 106 may be reduced. Once placed, the clinician may wish to trim the post 106. This may prevent the post 106 from contacting the external auditory canal.

Bilayer Tympanic Membrane Graft Insertion Devices and Grafts—Materials and Manufacture The device 100 can be made of one or more materials. For example, the device 100 can be made of a material or materials that are flexible under pressure from a tool such as forceps, but that return their original shape when that pressure is removed. Examples of such materials include, but are not limited to, at least one or more of polydimethylsiloxane (PDMS), hyaluronic acid (HA), poly(glycolic acid) (PGA), poly (lactic-co-glycolic acid) (PLGA), polylactic acid (PLA), polyurethane, collagen, fibrin, nylon, silk, poliglecaprone, poly(ester urethane)urea (PEUU), poly(carbonate urethane) urea (PECUU) and/or elastin. As described above, the device 100 can be made from a biodegradable material. This may be desirable, for instance, because the device 100 may not need to be removed if made of a biodegradable material. Alternatively, some materials can be dissolved with the application of a dissolving agent and such materials can also be used to make the new devices.

Materials with biodegradable properties, such as those listed herein, can serve to maintain the underlay and overlay grafts in position during the critical post-procedure healing period. This period can last between 1 week and 4 weeks and depends upon the patient's perforation size and underlying health of the middle ear. Surgeons can choose to select the material based upon the length of expected healing. Biodegradable materials used for the device 100 can resorb through normal blood flow and degradation through the middle and external ear, or can be expedited through the application of ototopical drops. For example, the pH of such drops can be selected to be low, such as acetic acid (vinegar), which can expedite the degradation of certain polymers such as polylactic acid or polyurethane. In another example, isopropyl alcohol could be used topically to reinforce a device 100 if a longer duration of placement is necessary.

In the case where, for example, a) a device 100 requires additional rigidity to support weight and orientation of the underlay and overlay grafts and/or b) a softer device 100 is needed to not further traumatize a perforated tympanic membrane, a solidifying agent can be used during or after placement in the ear canal. Alternatively, materials may be incorporated in the device 100 that solidify in response to the patient's body temperature. As an example, a device 100 may be soft at room temperature and become more rigid at body temperature. In another application, certain wavelengths of light, such as ultraviolet wavelength, can be used to cause the device 100 to harden. For example, a light with a specific wavelength can be introduced into the external auditory canal to solidify the device 100 further. In this regard, a relatively soft and pliable device 100 may be placed through the tympanic membrane, decreasing the potential for trauma to the tympanic membrane, and subsequently solidified.

Grafts delivered via the device 100 remain in place during the tympanic membrane healing process. Grafts have different degradation rates based upon their content. Autologous materials such as temporalis fascia or perichondrium can become incorporated into the fabric of the healed tympanic membrane, while non-autologous materials, such as porcine intestinal submucosa, degrades over time leaving a healed tympanic membrane behind. Grafts can be pre-populated with living cells such as fibroblasts, or may be autologous grafts and can still be populated with cells, such as in the case of a split thickness skin graft. The underlay graft and overlay graft need not necessarily be the same material. For example in one iteration an underlay graft of temporalis fascia could be used while the overlay split thickness skin graft could provide an epithelialized, cellularized material.

In some cases, the device 100 can include materials to aid in the healing of the tympanic membrane after graft placement. For example, the device 100 can include one or more living cells, such as living fibroblasts, chondrocytes, keratinocytes, and/or epithelial cells, in a scaffold material that enables the cells to thrive and reproduce once implanted. The device 100 can include one or more growth factors including, but not limited to, fibroblast growth factor (FGF), vascular endothelial growth factor (VEGF), and platelet-derived growth factor (PDGF), epidermal growth factor (EGF). The device 100 can include drugs and drug eluting material. For example, antibiotics and/or steroids can be used to aid in graft acceptance and/or healing. The manufacture of such devices can depend upon the shape and materials of the device 100. For example, the manufacture of the device 100 can include injection molding, three-dimensional printing, and/or the application of drugs, cells, or other materials.

The graft material or materials used with the device 100 can include any graft material appropriate for use in tympanoplasty used now or discovered in the future. These materials include organic tissue such as those harvested from the patient or a different donor, or artificial grafts. The grafts may themselves include or be treated with materials to aid in the healing of the tympanic membrane after graft placement, such as those described above. For example, grafts can be created from standard allograft materials such as temporalis fascia, perichondrium, fat, or skin grafts. Such allografts may be harvested at the time of surgery and can be prepared in a standard fashion. Underlay and overlay grafts do not necessarily have to be the same material.

The graft may also be any appropriate artificial graft, such as the graft materials described throughout PCT/US2016/023482, entitled "ARTIFICIAL TYMPANIC MEMBRANE DEVICES AND USES," which is incorporated herein by reference in its entirety. For example, artificial tympanic membrane grafts can be created by 3D printing a scaffold, e.g., in a 2D or 3D layer, made of ribs, with voids between the ribs. An infill material is typically used to fill the voids and to create a solid, optionally semipermeable, artificial tympanic membrane graft. To form the scaffold, ribs are formed in circular, or nearly circular, shapes. In addition, some of the ribs of the scaffold can be formed in straight or nearly straight shapes arranged in a radial pattern. Alternatively, some of the ribs of the scaffold can form a hub and spoke arrangement, while some other ribs of the scaffold can be formed in a group of concentric geometric shapes.

Between the ribs of the scaffold are voids. The voids are areas without any material of the scaffold. One or more materials can be used to fill the voids of the scaffold. The infill material can be selected to be biocompatible, capable of filling voids in a scaffold, and possessing the necessary mechanical properties to facilitate the transmission of vibrations to the patient once implanted. The material used can include some or all of the materials used in printing scaffolds.

EXAMPLE

The invention is further described in the following example, which does not limit the scope of the invention described in the claims.

Implantation of a Bilayer Tympanic Membrane Graft Insertion Device

The bilayer tympanic membrane grafts described herein were tested in human cadaver heads to simulate placement in the clinical setting. A cadaveric left ear was cleaned with betadine. A small-post-auricular incision was made. The dissection was taken down to the temporalis fascia. After the fascia was identified, a small retractor was utilized to expose the lateral surface of the true temporalis fascia. A piece of fascia of about 1.5 cm×1.5 cm was harvested using a Brown forceps and iris scissors. The fascia graft was then cleaned of any remaining muscle, divided into two components and allowed to desiccate. The post-auricular incision was closed in layered fashion, including 3-0 Vicryl® (polyglactin 910) and 4-0 Monocryl® (poliglecaprone 25) suture.

Using a 0 degree 14 cm endoscope, the middle ear cavity, including tympanic membrane, was visualized. Next, using a monopolar cautery a perforation was created in the posterior-inferior aspect of the tympanic membrane, which was measured as about 3 mm in diameter. The edges of the perforation were freshened with a Rosen pick and small cups forceps. This manually created perforation approximated a typical perforation seen in many patients.

Next, the bilayer tympanic membrane graft insertion device was assembled. First, the previously separated temporalis fascia was removed from the drying block. The fascia was incised with a 5 mm biopsy punch in the center of each graft, which creates the underlay and overlay grafts. Each graft was then perforated in the center using a Rosen needle to create a tiny hole to accommodate the graft delivery post (100). Using an alligator forceps, one piece of fascia was loaded on the post of the bilayer tympanic membrane graft device, placing the post 106 of the device through the small perforation in the underlay graft.

The loaded graft delivery device (100) was then placed in the "constrained configuration" using the alligator forceps to prepare for delivery and repair of the perforation. Using direct visualization from the endoscope, the underlay and arms 102 and 104 of the graft delivery post were placed through the tympanic membrane perforation. The post was pulled back slightly allowing for the full surface of the graft to lay flay on the medial (under) surface of the drum.

Next, the overlay graft was grasped with an alligator forceps. The next piece of facia was held by an alligator forceps and brought into the ear canal. This piece was placed so that the post extended through the central hole. The fascia graft was stably fixated on the lateral surface of the tympanic membrane by passing it over the shelf or shelf. This completed the assembly of the bilayer repair using the graft delivery post.

The angle of the post allowed it to sit comfortably without contacting the external auditory canal. The experiment demonstrated the necessary size specifications of both the device size and grafts. In addition, it demonstrated how a bilayer graft could be placed through the ear canal without further damage to the native and healthy tympanic membrane. This represents a feasible method of repairing tympanic membrane perforations without the need for large surgical procedures.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for holding an underlay graft and an overlay graft in place for repair of a tympanic membrane, the device comprising:
   a post having a proximal end and a distal end;
   first and second arms, each having a proximal end and a distal end; wherein the distal end of the post is flexibly joined to the proximal end of the first arm and to the proximal end of the second arm, and
   a shelf having a proximal end and a distal end, wherein the proximal end of the shelf is joined to the post between the proximal end and the distal end of the post such that, when the device is in a deployed configuration, the shelf extends substantially perpendicularly from the post and is substantially perpendicular to the first arm and the second arm;
   wherein, when the device is in a deployed configuration, the first arm and the second arm extend substantially perpendicularly from the post; and when the first arm and the second arm are clamped into a constrained configuration, the first arm and the second arm extend substantially in parallel to a central axis of the post.

2. The device of claim 1, wherein the device comprises a biodegradable material.

3. The device of claim 1, wherein the device comprises one or more of polydimethylsiloxane (PDMS), hyaluronic acid (HA), poly(glycolic acid) (PGA), poly (lactic-co-glycolic acid) (PLGA), polylactic acid (PLA), polyurethane, poly(ester urethane)urea (PEUU), poly(carbonate urethane)urea (PECUU), collagen, fibrin, nylon, silk, poliglecaprone, and elastin.

4. The device of claim 1, wherein the device comprises at least one of a cellular adhesion-inducing material and a cellular invasion-inducing material.

5. A device for holding an underlay graft and an overlay graft in place for repair of a tympanic membrane, the device comprising:
   a post having a proximal end and a distal end; and
   first and second arms, each having a proximal end and a distal end; wherein the distal end of the post is flexibly joined to the proximal end of the first arm and to the proximal end of the second arm;
   wherein, when the device is in a deployed configuration, the first arm and the second arm extend substantially perpendicularly from the post and when the first arm and the second arm are clamped into a constrained configuration, the first arm and the second arm extend substantially in parallel to a central axis of the post,
   further comprising one or more living fibroblasts, chondrocytes, keratinocytes, and/or epithelial cells in a scaffold material that enables the cells to thrive and reproduce once implanted.

6. The device of claim 1, further comprising one or more growth factors.

7. The device of claim 6, wherein the growth factor comprises one or more of fibroblast growth factor (FGF), vascular endothelial growth factor (VEGF), and platelet-derived growth factor (PDGF), epidermal growth factor (EGF).

8. The device of claim 1, further comprising at least one or more of a drug and drug eluting material.

9. A method of repairing a perforation in a tympanic membrane, the method comprising:
   loading the underlay graft on a device comprising:
   a post having a proximal end and a distal end; and
   first and second arms, each having a proximal end and a distal end; wherein the distal end of the post is flexibly joined to the proximal end of the first arm and to the proximal end of the second arm;
   wherein, when the device is in a deployed configuration, the first arm and the second arm extend substantially perpendicularly from the post and when the first arm and the second arm are clamped into a constrained configuration, the first arm and the second arm extend substantially in parallel to a central axis of the post;
   clamping the first and second arms into the constrained configuration to cause the first and second arms to extend substantially parallel to a central axis of the post;
   passing i) the first arm, ii) the second arm, iii) the distal end of the post, and iv) the underlay graft from a lateral side of the tympanic membrane to a medial side of the tympanic membrane through the perforation;
   releasing the first and second arms from the constrained configuration to hold the underlay graft in contact with a medial surface of the tympanic membrane; and
   loading the overlay graft on the device such that the overlay graft is in contact with the lateral side of the tympanic membrane.

10. The method of claim 9, the method further comprising removing the device by pulling the post member out through the remaining perforation after the tympanic membrane has healed at least a portion of the perforation.

11. The method of claim 9, wherein the method further comprises dissolving the device by application of a dissolving agent.

12. The method of claim 9, wherein the method further comprises solidifying the device by application of a solidifying agent.

13. The method of claim 9, wherein loading the underlay graft on the device comprises passing the distal end of the post through a hole in the underlay graft.

14. The method of claim 9, wherein the device further comprises a shelf having a proximal end and a distal end, wherein the proximal end of the shelf is joined to the post between the proximal end and the distal end of the post such that, when the device is in a deployed configuration, the shelf extends substantially perpendicularly from the post and is substantially perpendicular to the first arm and the second arm.

15. A system for holding an underlay graft and an overlay graft in place for repair of a tympanic membrane, the system comprising:
   (a) a device comprising:
      (i) a post having a proximal end and a distal end; and
      (ii) first and second arms, each having a proximal end and a distal end;
      wherein the distal end of the post is flexibly joined to the proximal end of the first arm and to the proximal end of the second arm;
      wherein, when the device is in a deployed configuration, the first arm and the second arm extend substantially perpendicularly from the post; and when the first arm and the second arm are clamped into a constrained configuration, the first arm and the second arm extend substantially parallel to a central axis of the post;
   (b) an underlay graft comprising a hole and being loaded onto the device such that the post passes through the hole; and
   an overlay graft comprising a second hole.

16. The system of claim 15, wherein the overlay graft is loaded onto the device such that the post passes through the second hole.

17. A system for holding an underlay graft and an overlay graft in place for repair of a tympanic membrane, the system comprising:
  (a) a device comprising:
    (i) a post having a proximal end and a distal end; and
    (ii) first and second arms, each having a proximal end and a distal end; wherein the distal end of the post is flexibly joined to the proximal end of the first arm and to the proximal end of the second arm; and
    (iii) a shelf having a proximal end and a distal end, wherein the proximal end of the shelf is joined to the post between the proximal end and the distal end of the post such that, when the device is in a deployed configuration, the shelf extends substantially perpendicularly from the post and is substantially perpendicular to the first arm and the second arm;
    wherein, when the device is in a deployed configuration, the first arm and the second arm extend substantially perpendicularly from the post and when the first arm and the second arm are clamped into a constrained configuration, the first arm and the second arm extend substantially parallel to a central axis of the post; and
  (b) an underlay graft comprising a hole and being loaded onto the device such that the post passes through the hole.

18. The system of claim 17, wherein the underlay graft rests on the post between the shelf and the first and second arms.

* * * * *

UNITED STATES PATENT AND TRADEMARK OFFICE
CERTIFICATE OF CORRECTION

PATENT NO. : 10,799,341 B2
APPLICATION NO. : 16/333698
DATED : October 13, 2020
INVENTOR(S) : Aaron K. Remenschneider and Elliott Kozin It is certified that error appears in the above-identified patent and that said Letters Patent is hereby corrected as shown below:

In the Specification

In Column 2, Line 4-5, delete "poly(carbonate urethane)" and insert -- poly(ester carbonate urethane) --

In Column 3, Line 9, delete "poly(carbonate urethane)" and insert -- poly(ester carbonate urethane) --

In Column 8, Line 14-15, delete "poly(carbonate urethane)" and insert -- poly(ester carbonate urethane) --

In the Claims

In Column 11, Line 32, Claim 3, delete "poly(carbonate urethane)" and insert -- poly(ester carbonate urethane) --

In Column 11, Line 48, Claim 5, delete "post" and insert -- post; --

In Column 12, Line 8, Claim 9, delete "post" and insert -- post; --

In Column 13, Line 22, Claim 17, delete "post" and insert -- post; --

Signed and Sealed this
Fifteenth Day of December, 2020

Andrei Iancu
*Director of the United States Patent and Trademark Office*